(12) United States Patent
Petiot et al.

(10) Patent No.: US 9,220,626 B2
(45) Date of Patent: Dec. 29, 2015

(54) SUPPORT DEVICE, IN PARTICULAR FOR GIVING LUMBAR SUPPORT

(75) Inventors: Séverine Petiot, Roche la Moliere (FR); Henri De Moncuit, Saint Etienne (FR)

(73) Assignee: THUASNE S.A., Levallois Perret (FR)

( * ) Notice: Subject to any disclaimer, the term of this patent is extended or adjusted under 35 U.S.C. 154(b) by 1165 days.

(21) Appl. No.: 12/996,558

(22) PCT Filed: Jun. 9, 2009

(86) PCT No.: PCT/FR2009/051085
§ 371 (c)(1),
(2), (4) Date: Jan. 4, 2011

(87) PCT Pub. No.: WO2010/001030
PCT Pub. Date: Jan. 7, 2010

(65) Prior Publication Data
US 2011/0112453 A1    May 12, 2011

(30) Foreign Application Priority Data

Jun. 9, 2008 (FR) ...................... 08 53805

(51) Int. Cl.
| *A61F 5/00* | (2006.01) |
| *A61F 5/02* | (2006.01) |
| *A61F 5/01* | (2006.01) |
| A61F 5/03 | (2006.01) |
| A41C 1/00 | (2006.01) |
| A41C 1/14 | (2006.01) |

(52) U.S. Cl.
CPC . *A61F 5/028* (2013.01); *A61F 5/00* (2013.01); *A61F 5/01* (2013.01); *A61F 5/02* (2013.01); *A41C 1/00* (2013.01); *A41C 1/14* (2013.01); *A61F 5/03* (2013.01)

(58) Field of Classification Search
CPC .............. A61F 5/00; A61F 5/01; A61F 5/02; A61F 5/028; A61F 5/03; A41C 1/00; A41C 1/02; A41C 1/08; A41C 1/12; A41C 1/14; Y10T 24/314; Y10T 24/316; Y10T 24/1394; Y10T 24/4088
USPC .............. 602/19; 450/94, 109, 114, 115, 122, 450/123, 143, 146, 2, 96; 2/44, 311, 338, 2/92, 467; 128/875, 876, 869; 224/660
See application file for complete search history.

(56) References Cited

U.S. PATENT DOCUMENTS

| 1,893,960 A | 1/1933 | Pease |
| 3,717,143 A | 2/1973 | Johnson |

FOREIGN PATENT DOCUMENTS

| DE | 23 34 500 A1 | 1/1975 |
| FR | 2 687 912 A | 9/1993 |
| GB | 136 409 A1 | 12/1919 |
| WO | 2007129950 A1 | 11/2007 |

*Primary Examiner* — Kim M Lewis
*Assistant Examiner* — Keri J Nelson
(74) *Attorney, Agent, or Firm* — Kenyon & Kenyon LLP

(57) ABSTRACT

The present invention relates to a support device, in particular for giving lumbar support, which device comprises an elastic belt provided, at its ends, with complementary closure means, and at least one elongate side reinforcing element that is fastened over the height of the belt. In characteristic manner, over a fraction of its length, the belt has elasticity that varies over the height thereof, so that extending the belt longitudinally causes the elongate reinforcing element to shift angularly towards a respective one of the ends of the belt.

10 Claims, 4 Drawing Sheets

SUPPORT DEVICE, IN PARTICULAR FOR GIVING LUMBAR SUPPORT

This is a 371 national phase application of PCT/FR2009/051085 filed 9 Jun. 2009, claiming priority to French Patent Application No. 0853805 filed 9 Jun. 2008, the contents of which are incorporated herein by reference.

FIELD OF THE INVENTION

The present invention relates to the technical field of support devices, in particular for giving lumbar support, such a device comprising an elastic belt provided, at its ends, with complementary closure means.

BACKGROUND OF THE INVENTION

A support device, in particular for giving lumbar support, is adapted to the morphology of the patient and to the pathology to be treated, in particular for supporting the back at the base of the spine and in the small of the back. In order to perform its support function, the belt is provided with reinforcing elements, which are generally stays made of a malleable metal or of synthetic resins, and which are often sewn onto the belt in a slightly inclined position so as to follow the outlines connecting the hips to the waist. Such reinforcing elements are fastened to the belt at angles of inclination determined by the manufacturer regardless of the morphology of the patient, e.g. in a V-shaped configuration. With state-of-the-art belts, it is not possible to obtain customized support by allowing the reinforcing elements to take up inclinations as a function of the morphology of the patient when the patient adjusts and then closes the belt around the waist. Such reinforcing elements that do not adapt to the unique morphology of each patient (as a function of height, weight, sex, etc.) can be uncomfortable, in particular when worn for prolonged periods, to the extent that the patient does not wear the belt for periods that are long enough and removes it early, or indeed does not tighten it enough. The desired therapeutic effect is then not achieved.

Document U.S. Pat. No. 1,893,960 discloses a support device, in particular for giving lumbar support, that comprises an elastic belt provided, at its ends, with complementary closure means, and a plurality of elongate reinforcing elements disposed over the height of the belt and having their bottom ends fastened to a rigid plate. When the belt is extended longitudinally, the top portions of the elongate reinforcing elements move apart in fanlike manner.

SUMMARY OF THE INVENTION

An object of the present invention is to provide a support device, in particular for giving lumbar support, that, compared with the device known from Document U.S. Pat. No. 1,893,960, improves the comfort of the patient.

This object is indeed achieved by the device of the present invention. The device provided by the present invention is a support device, in particular for giving lumbar support, which device comprises an elastic belt provided, at its ends, with complementary closure means, and at least two elongate side reinforcing elements that are fastened over the height of the belt, between which side reinforcing elements the longitudinal elasticity of the belt varies over the height thereof. In characteristic manner, said device further comprises a back panel that extends over the height of the belt and that has its top portion connected to the top ends only of said side reinforcing elements so as to act as a restraining piece suitable for limiting the extensibility of the belt so that extending the belt longitudinally causes the bottom ends of said elongate reinforcing elements to shift angularly towards respective ones of said ends of the belt.

The comfort of the patient is improved, firstly because of the presence of the back panel and of the absence of a rigid plate, and secondly because the side reinforcing elements take up inclinations adapted to the morphology of the patient, corresponding to the outlines connecting the hips to the waist.

The complementary closure means may be any closure means known from the state of the art, and they are preferably male and female members of the hook-and-loop type, the loops preferably being formed by a brushed velvet of the astrakhan cloth type.

The height of the belt is defined as being the (sometimes non-constant) distance between the top edge and the bottom edge of the belt.

"Extending the belt longitudinally" means that, while the patient is adjusting the belt to fit the waist, and while the patient is standing up, said patient exerts traction on each of the ends so as to bring said ends to co-operate together so as to close them and, by the same token, so as to tighten the belt.

Preferably, the elongate reinforcing elements are not elastic.

The elongate reinforcing elements may be in positions in which they are inclined slightly relative to the vertical of the patient while said patient is standing up, and is wearing the belt of the present invention. Preferably, the elongate reinforcing elements are connected to the back panel so that they extend substantially vertically relative to the vertical of the patient when said patient is standing up.

The elasticity is caused to vary over the height of the belt by the presence of the back panel, the top portion of which that interconnects the ends of the side reinforcing elements acts as a restraining piece over a portion of the height of the belt. At least in the longitudinal direction, said restraining piece has elasticity that is less than the longitudinal elasticity of the belt so that extending the belt longitudinally causes the reinforcing elements to shift angularly.

When the user adjusts the belt to fit the waist, said user exerts traction on each of the ends thereof, thereby generating traction forces that are exerted on either side of the reinforcing elements in varying manner, in a region of the length of the belt, by means of the elasticity of the belt varying in said region over the height of said belt. The less elastic first zone of said region restrains the adjacent portion of the reinforcing element. The traction force exerted on the more elastic second zone of said region lengthens said region to a greater extent than in the less elastic first zone, so that the adjacent portion of the corresponding reinforcing element follows the deformation of the more elastic second zone and is inclined towards one of the ends of the belt proportionally to the traction force exerted on said ends by the patient, and as a function of the morphology of the patient.

Preferably, the inclinable elongate reinforcing elements are offset symmetrically from the middle axis of the belt, so that when the user adjusts the belt to fit the waist and exerts traction on its ends to cause the closure means to co-operate, each reinforcing element is inclined towards the nearer end through the same angular shift.

Tests conducted on patients have shown the improvement in comfort procured by support devices of the present invention, and correlatively the improvement in the desired therapeutic effect because patients wear said devices for the prescribed times.

When the user adjusts the belt to fit the waist and exerts traction on each of its ends to cause the complementary closure means to co-operate, each of the side reinforcing elements is inclined towards the end of the belt that is nearer to it. The side reinforcing elements as inclined in this way take up directions that are substantially parallel to the outlines respectively connecting the right and left hips to the right and left sides of the waist.

The above-described region of varying elasticity, having a first zone, is disposed between said side reinforcing elements.

The side reinforcing elements may be fastened to the belt, e.g. by sewing or dielectric welding (of the ultrasound or high-frequency type). The side reinforcing elements may be in positions in which they are slightly inclined so as to form an upside-down V-shape, or preferably be substantially parallel and disposed vertically relatively to the vertical of the patient while said patient is standing up. The back panel is not fastened directly to the belt; it is fastened indirectly thereto via the side reinforcing elements that it secures together.

Since the bottom ends of the reinforcing elements are not restrained by the back panel, they are able to pivot towards respective ones of the ends of the belt so as to take up inclinations adapted to the morphology of the patient, and in particular to the hip-waist proportion defining the outlines connecting the hips to the waist.

Preferably, between the side reinforcing elements, the elasticity of the belt that varies over the height thereof increases going from the top edge to the bottom edge thereof.

Preferably, the back panel is secured to the belt in its top portion only, which top portion of the back panel is connected to the top ends of the side reinforcing elements. More particularly, the left and right edges of the back panel are secured respectively to the right edge of a first side reinforcing element and to the left edge of a second side reinforcing element.

In a variant, the back panel has two complementary elongate central reinforcing elements.

In a variant, each reinforcing element or each complementary elongate reinforcing element is a stay inserted into a sheath fastened over the height of the belt or over the height of the back panel.

In a variant, the back panel is connected to the side reinforcing elements over about one third of the total height thereof.

In a variant, the belt is made up of two extensible strips that, at respective ones of their ends, are provided with the complementary closure means, and that are secured together via said side reinforcing elements that are secured together at their top ends via said restraining part(s).

The number of side reinforcing elements is preferably even, and it is a function of comfort, cost, and desired support.

In a variant, the belt is made up of two extensible strips that converge towards the ends of said belt.

The angle of convergence of the strips is a function of the pathology to be treated.

Preferably, for improved and controlled angular pivoting, the belt further comprises an elastic return piece that is optionally made up of one or more elastic strips, and that is disposed between the side reinforcing elements. Said elastic piece may have elasticity that is uniform over its entire height, or that increases going from its top edge to its bottom edge.

In which case, the back panel is preferably arranged on the inside face of the device, and the elastic return piece is arranged on the outside face of the device, so as to cover all or some portion of the back panel while the device is being used.

BRIEF DESCRIPTION OF THE DRAWINGS

The invention can be understood more clearly from the following description of two preferred embodiments given by way of non-limiting example and with reference to the accompanying drawings, in which.

DETAILED DESCRIPTION

Figure 1:
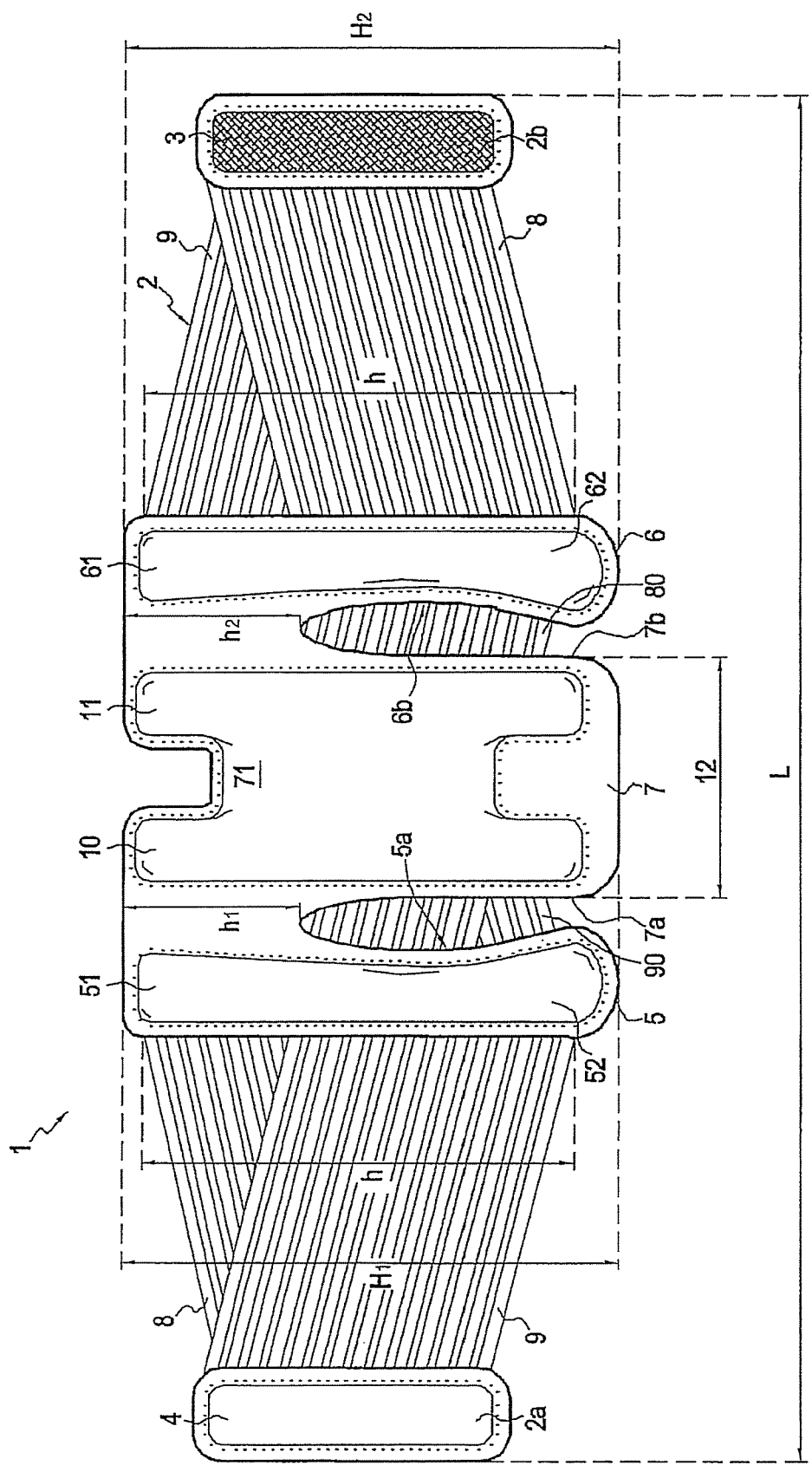
FIG. 1 is a view of the inside face of a first example of a device of the present invention as laid out flat.

The lumbar support device 1 shown in FIG. 1 comprises an elastic belt 2 provided, at its ends 2a, 2b, with complementary closure means 3, 4, preferably of the hook-and-loop fastener type. The support device 1 further comprises first and second elongate side reinforcing elements 5 and 6 that are disposed on either side of a back panel 7. The side reinforcing elements 5, 6 are fastened over the height h of the belt 2 by any means: sewing, ultrasound welding or high-frequency welding. The side reinforcing elements 5, 6 have respective determined heights H1 and H2 that are preferably of the same order. On either side of the two side reinforcing elements 5, 6, the belt 2 comprises two extensible strips 8, 9 that converge from the two side reinforcing elements 5, 6 towards its ends 2a, 2b. The belt 2 is thus extensible from one end to the other. The back panel 7 extends over the height h of the belt 2 and comprises two elongate central reinforcing elements 10, 11. The right edge 7a and the left edge 7b of the back panel 7 are respectively connected to the left edge 5a of the first side reinforcing element 5 and to the right edge 6b of the second side reinforcing element 6, at the top ends 51, 61 of said side reinforcing elements 5, 6. In this precise example, the back panel 7 is connected to each of the side reinforcing elements 5, 6 over about one third of the total height H1, H2 of the side reinforcing element, corresponding to a respective one of the heights h1 and h2. The side reinforcing elements 5, 6, and the central reinforcing elements 10, 11 are stays inserted into sheaths fastened over the height respectively of the belt 2 and of the back panel 7. The back panel 7 covers a given region 12 of the length L of the belt 2 corresponding to a restraining first zone 71. In this precise example, the first zone 71 and the region 12 are substantially centered over the length L of the belt 2. The back panel 7 substantially has elasticity, and in particular a modulus of elasticity E1, that is less than the elasticity of the extensible strips 8, 9, and in particular less than the respective moduli of elasticity E2 and E3 thereof. Preferably, the back panel 7 and the side reinforcing elements 5, 6 are not elastic. The first zone 71 of the back panel 7 thus restrains elongation of the extensible strips 8, 9 in said region 12 at the top ends 51, 61 of the side reinforcing elements 5, 6 so that said first zone 71 of the back panel 7 acts as a restraining piece and makes it possible to cause the longitudinal elasticity of the belt 2 to vary over its height h.

In this precise example, the side reinforcing elements 5, 6 are parallel and are disposed vertically relative to the vertical of the patient when said patient is standing up, and when the belt is not extended.

Preferably, the side sheaths in which the side reinforcing elements 5, 6 are received are made of a material that is less elastic than the extensible strips 8, 9, and that is optionally similar to the material of which the central sheaths are made. Preferably, said material is a textile, in particular a three-dimensional fabric having its inside face, i.e. its face designed to be in contact with the user, provided with openings of size of about one millimeter for the purpose of facilitating removal of heat and of moisture.

Figure 2:
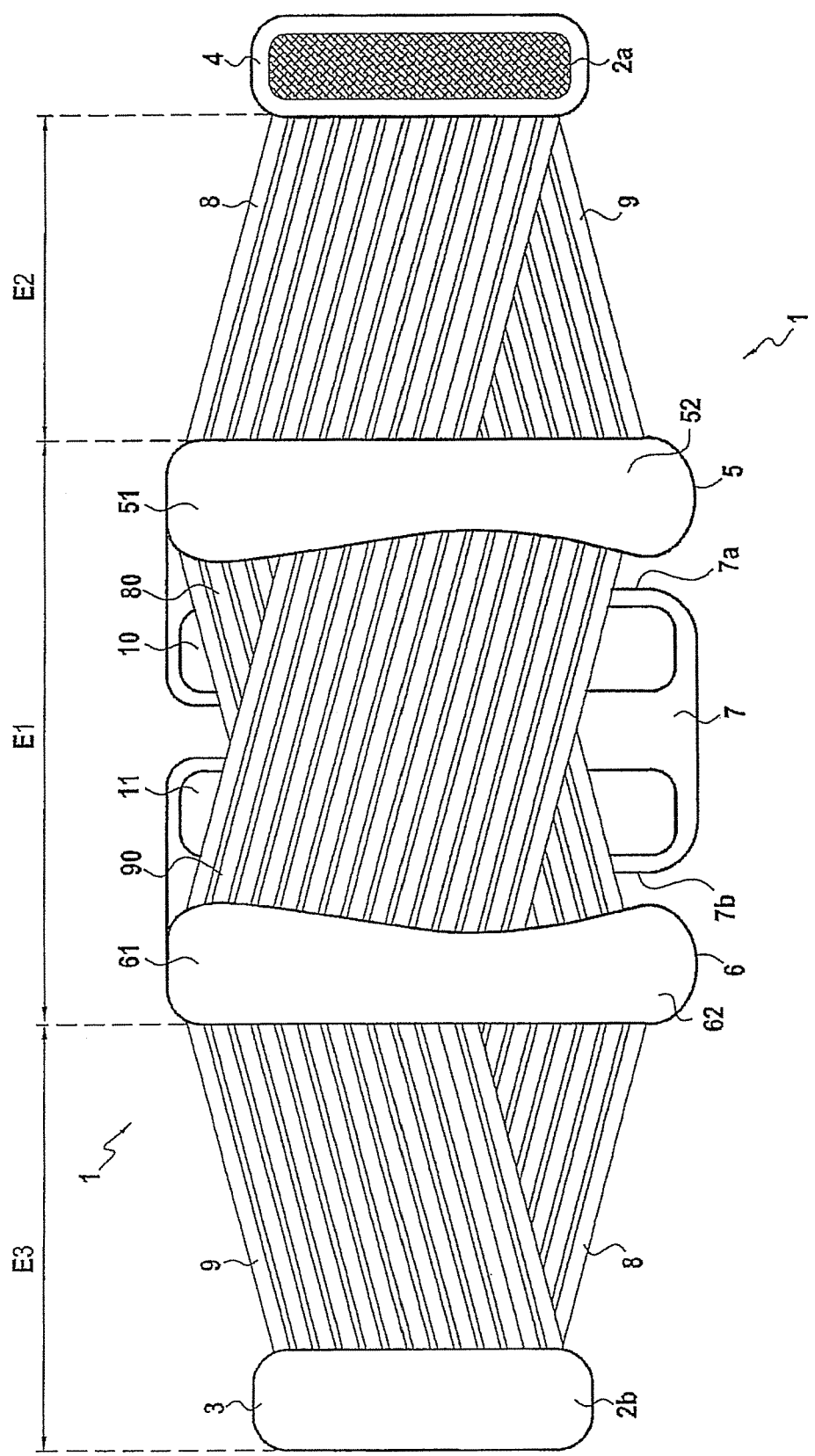
FIG. 2 is a view of the outside face of the device shown in FIG. 1.
Figure 3:
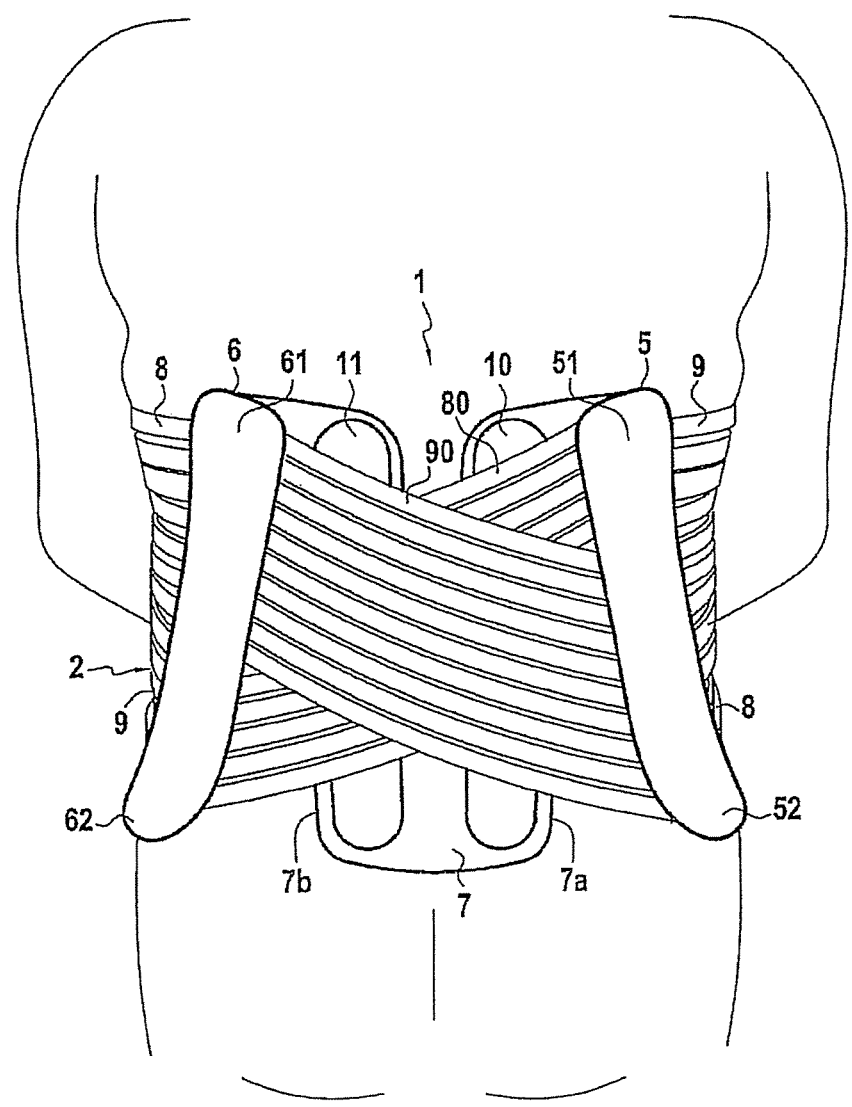
FIG. 3 is a perspective view of the device shown in FIGS. 1 and 2 as worn by a patient.

Preferably, as shown in FIGS. 1 to 3, the two side reinforcing elements 5, 6 are interconnected via an elastic return piece that, in this precise example, is made up of two extensible strips 80, 90 that cross over each other. This piece is designed to control the angular pivoting of the two side reinforcing elements 5, 6. It may have elasticity that is uniform over its entire height. It may also have elasticity that increases going from its top edge to its bottom edge, which constitutes an intermediate solution between having no return piece at all, and having a return piece that is of uniform elasticity over its entire height, with regard to the force to be exerted to obtain pivoting through a given angle.

The side reinforcing elements 5, 6 of the back panel 7 are arranged on the inside face of the device 1, i.e. on its face facing towards the user while it is being used. The elastic return piece 80, 90 is arranged on the outside face of the device and it covers all or some portion of the back panel 7. Thus, the return piece presses the back panel against the back, improving the dorsal reinforcement without limiting the freedom of movement of the bottom ends of the side reinforcing elements.

Figure 4:
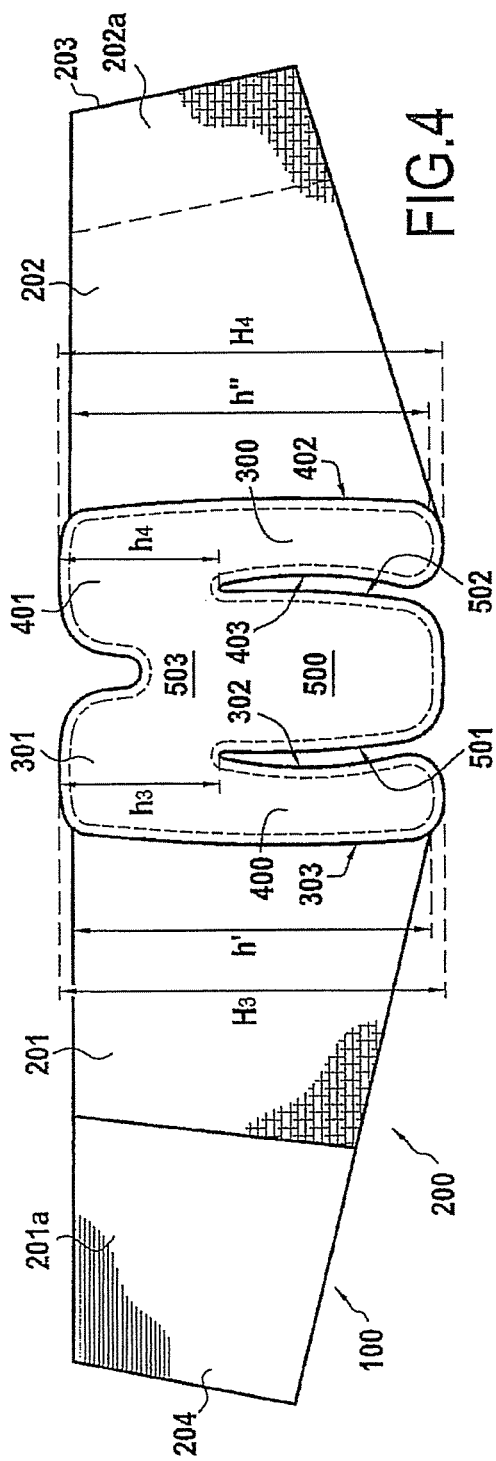
FIG. 4 is a view of the inside face of a second example of a device of the present invention, as laid out flat.
Figure 5:
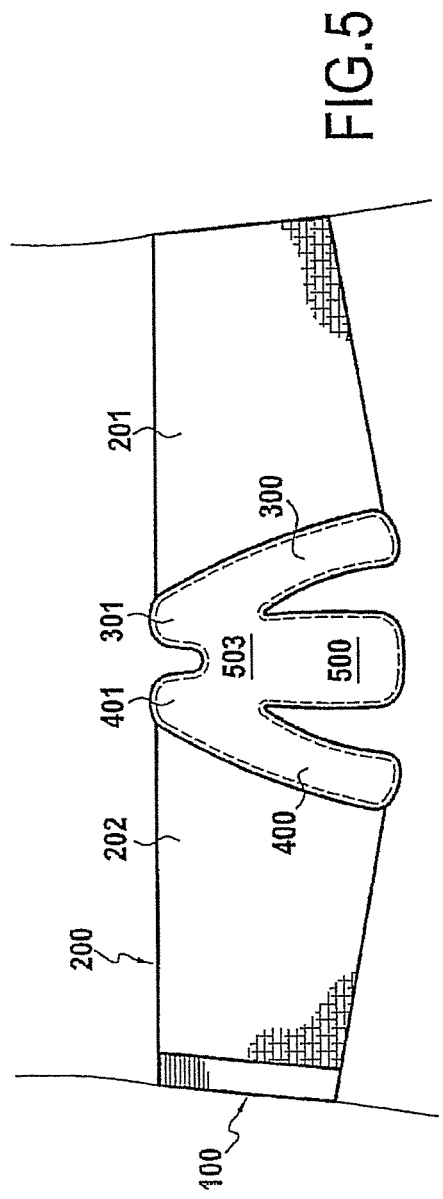
FIG. 5 is a view of the second example of a device shown in FIG. 4 as worn by a patient.

In operation, the user places the belt 2 around the waist and the hips, and then exerts traction on each of the ends 2a, 2b of the belt. The traction forces exerted at the ends 2a, 2b of the belt 2 propagate to the side reinforcing elements 5, 6. Since the top ends 51, 61 of the side reinforcing elements 5, 6 are restrained by the first zone 71 of the back panel 7 that acts as a restraining piece, the bottom ends 52, 62 of the side reinforcing elements 5, 6 pivot angularly about their axes at their top ends 51, 61, each bottom end pivoting towards the closer of the ends 2a, 2b of the belt 2. The patient closes the belt 2 by causing the closure means 3, 4 to co-operate with each other. The first and second side reinforcing elements 5, 6 then extend respectively in directions that are substantially parallel to the outlines connecting the left and right hips to the left and right sides of the waist, as shown in FIG. 3. This configuration of the side reinforcing elements 5, 6 corresponds to an upside-down V-shape. The side reinforcing elements 5, 6 are angularly positioned as a function of the morphology of the patient, and in particular as a function of the ratio between the measurements of the hips and of the waist, thereby significantly improving the comfort of the patient. The simplified second example of a lumbar support device 100 that is shown in FIGS. 4 and 5 differs from the device 1 in that it comprises a belt 200 that, on either side of the two side reinforcing elements 300, 400, has a single extensible strip 201, 202 that, at its end 201a, 202a, has complementary closure means 203, 204, and does not have any elastic return piece. The strips 201, 202 are interconnected via two elongate side reinforcing elements 300, 400 that are secured at their top ends 301, 401 to a back panel 500 acting as a restraining piece. The back panel 500 may be made up of a single elongate reinforcing element, or else of two complementary elongate reinforcing elements.

The heights H3, H4 of the side reinforcing elements 300, 400 are about the same as the heights h', h" of the extensible strips 201, 202.

In the same way as for the device 1, the right edge 501 and the left edge 502 of the back panel 500 are connected respectively to the left edge 302 of the first side reinforcing element 300 and to the right edge 403 of the second side reinforcing element 400, at the top ends 301, 401 of said side reinforcing elements 300, 400. In this precise example, the back panel 500 is connected to each of the side reinforcing elements 300, 400 over about one third of the total height H3, H4 of the side reinforcing element, corresponding to a respective one of the heights h3 and h4.

In operation, with the side reinforcing elements 300, 400 being, in this precise example that is shown in FIG. 5, free over two-thirds of their heights H3, H4, respectively along the left edge 302 and along the right edge 403, then when the patient adjusts the belt 200 to fit the waist, said side reinforcing elements 300, 400 pivot about their top ends 301, 401 and about the restraining first zone 503 so as to take up the outlines connecting the hips to the sides of the waist complying with the patient's unique morphology.

The invention claimed is:

1. A support device configured to give lumbar support, which device comprises an elastic belt having ends, wherein the end of said elastic belt are provided with complementary closure means, and said support device comprises at least two elongate side reinforcing elements that are fastened over the height of the belt, the longitudinal elasticity of the belt varying over the height thereof, wherein said support device further comprises a back panel that extends over the height of the belt and that has a top portion and bottom portion, wherein when the support device is worn by the user the top portion of the back panel supports at least in part the back that is above the waist and the bottom portion of the back panel supports at least in part the back that is under the waist, wherein the back panel is secured to the belt in its top portion only, which top portion of the back panel is connected to the top ends of said side reinforcing elements so as to act as a restraining piece suitable for limiting the extensibility of the belt so that extending the belt longitudinally causes the bottom ends of said elongate reinforcing elements to shift angularly towards respective ones of said ends of the belt.

2. A device according to claim 1, wherein, between the side reinforcing elements, the elasticity of the belt that varies over the height thereof increases going from the top edge to the bottom edge thereof.

3. A device according to claim 1, wherein the side reinforcing elements are secured together at their top ends only, via the back panel.

4. A device according to claim 1, further comprising an elastic return piece that is optionally made up of one or more elastic strips, and that is disposed between the side reinforcing elements.

5. A device according to claim 4, wherein the back panel is arranged on an inside face of the device, and the elastic return piece is arranged on an outside face of the device, so as to cover all or some portion of the back panel while the device is being used.

6. A device according to claim 1, wherein the back panel is made up of two complementary elongate reinforcing elements that are fastened over the height of the back panel.

7. A device according to claim 1, wherein each reinforcing element and/or each complementary elongate element is a stay inserted into a sheath fastened over the height of the belt or over the height of the back panel.

8. A device according to claim 1, wherein the back panel is connected to the side reinforcing elements over about one third of the total height thereof.

9. A device according to claim 1, wherein the belt is made up of two extensible strips that, at respective ones of their ends, are provided with the complementary closure means, and, at their respective other ends, are secured to respective ones of the two side reinforcing elements.

10. A device according to claim 9, wherein the belt is made up of two extensible strips that converge towards the ends of said belt.

* * * * *